(12) United States Patent
Scherf et al.

(10) Patent No.: US 6,419,797 B1
(45) Date of Patent: Jul. 16, 2002

(54) METHOD FOR PRODUCING METAL-FREE GUERBET ALCOHOLS

(75) Inventors: Erich Scherf; Hans-Jürgen Letsch, both of Brunsbüttel; Clemens Schröder, Kayhude; Albert Thomas Herrmann, Brunsbüttel, all of (DE)

(73) Assignee: Sasöl Germany GmbH (DE)

( * ) Notice: Subject to any disclaimer, the term of this patent is extended or adjusted under 35 U.S.C. 154(b) by 0 days.

(21) Appl. No.: 09/485,574

(22) PCT Filed: Aug. 7, 1998

(86) PCT No.: PCT/DE98/02345

§ 371 (c)(1),
(2), (4) Date: Feb. 11, 2000

(87) PCT Pub. No.: WO99/07661

PCT Pub. Date: Feb. 18, 1999

(30) Foreign Application Priority Data

Aug. 11, 1997 (DE) .......................... 197 34 673

(51) Int. Cl.⁷ .......................... B01D 3/10; C07C 29/34; C07C 29/80
(52) U.S. Cl. .............. 203/74; 203/77; 203/80; 203/88; 568/905; 568/913
(58) Field of Search .................. 203/72, 71, 73, 203/100, 74, 77, 80, 88, 29; 568/905

(56) References Cited

U.S. PATENT DOCUMENTS 4,011,273 A    3/1977   Abend et al. ............... 568/715
5,777,183 A  * 7/1998   Mueller et al. ............ 568/905

FOREIGN PATENT DOCUMENTS

| DE | 2703746 | 8/1985 |
| DE | 4014736 | 11/1991 |
| DE | 119531714 | 5/1996 |
| GB | 1433986 | 4/1976 |
| WO | WO 91/04242 | 4/1991 |

OTHER PUBLICATIONS

Anthony J. O'Lenick, Jr. and Raymond E. Bilbo, "Guerbet Alcohols: A Versatile Hydrophobe," Soap/Cosmetics/Chemical Specialties, Apr., 1987, pp. 52, 54–55, and 115.

* cited by examiner

Primary Examiner—Virginia Manoharan
(74) Attorney, Agent, or Firm—Browning Bushman P.C.

(57) ABSTRACT

There is provided a process for producing Guerbet alcohols not containing any heavy metals or soaps, wherein primary and/or secondary alcohols having 2 to 30 carbon atoms are condensed at elevated temperature in the presence of alkaline catalysts and/or heavy metal catalysts while eliminating the reaction water, and the reaction product is immediately separated by distillation without any additional purification.

13 Claims, No Drawings

METHOD FOR PRODUCING METAL-FREE GUERBET ALCOHOLS

BACKGROUND OF THE INVENTION

1. Field of the Invention

The present invention relates to a process for producing high-purity Guerbet alcohols by condensation of primary and/or secondary alcohols having 2 to 30 carbon atoms in the presence of one or more alkaline catalyst(s) and/or one or more heavy metal catalyst(s).

2. Description of the Prior Art

Guerbet alcohols are known compounds used as base materials for a large number of applications, e. g. in the cosmetic, pharmaceutical, textile and lubricants industries.

Guerbet alcohols can be produced by condensation of primary and secondary alcohols in the presence of strong alkali bases according to the following reaction scheme:

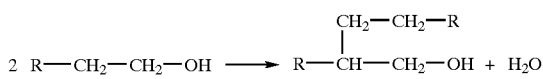

There exist a large number of catalyst systems based on alkali/alkaline earth salts in the presence of heavy metals as co-catalysts.

Among alkaline catalysts, alkali metals, alkali metal hydroxides, alkali metal oxides and alkali metal alcoholates are known. Furthermore, there have been described combinations, such as KOH with ZnO. However, such combinations often have specific disadvantages (see e. g. Soap/Cosmetics/Chemical Specialties, pages 52–55 and 115, April 1987).

Among heavy metals as co-catalysts, there have been described ZnO, PbO, NiO, Pd, Ti and Zr compounds. A large number of useful co-catalysts have been described in German Patent Specification DE 24 00 326. According to German Patent Specification DE 26 34 676, insoluble salts of the group of lead silicates, lead titanates, and lead zirconates(IV) in the presence of alkali bases can also be used as catalysts.

In addition, known co-catalysts are those based on ZnO and insoluble lead salts of the group of lead silicates, lead titanates, and lead zirconates(IV). The lead salts may have discretionary ratios of PbO to $SiO_2$, $TiO_2$, or $ZrO_2$ resulting in different basicities of the co-catalysts.

Furthermore, it is known to use heterogeneous catalyst systems, e. g. those consisting of platinum supported on activated carbon having a large surface and potassium or sodium hydroxide.

Although suitable catalyst systems can significantly increase rate and yield of the alcohol reaction providing Guerbet alcohols, the heavy metal salts used require careful separation and disposal because of their detrimental effect to the environment.

There exists yet another problem, that is the crude product obtained by Guerbet reaction normally contains by-products, such as aldehydes, unsaturated compounds and, especially, soaps in different quantities. It is particularly important that the soaps contained in the reaction mixture which are soluble and insoluble at room temperature be separated after the reaction is complete. Said soaps are usually separated by washing with partially acidified aqueous solutions, e. g. 6% sodium chloride solution (DE A1 26 34 676). This treatment produces large quantities of waste water also containing the heavy metals. Subsequent precipitation and separation of said heavy metals used as catalysts or co-catalysts will involve considerable costs. Moreover, using aqueous solutions for this washing treatment has another disadvantage, that is waste water having a high content of organic materials will be obtained and, additionally, the Guerbet alcohols yield will decrease. A theoretical solution to this problem would be using a solid carrier, e. g. activated carbon, for the co-catalysts which can be separated by filtration after the reaction is complete. In practice, however, the supports were found to undergo mechanical and chemical decomposition during the reaction so that complete separation by simple filtration will not produce the desired result. Furthermore, the production of supported co-catalysts instead of employing the transition metal salts and oxides commonly used would result in considerably higher costs.

In order to avoid the problems mentioned hereinabove, it has been suggested in DE 195 31 714 to eliminate the soaps which are difficultly soluble at room temperature by filtration, centrifugation and/or extraction and subsequent distillation. However, the filter cake produced during filtration will increase the amount of waste and the extraction with water will produce waste water having a high content of heavy metals.

SUMMARY OF THE INVENTION

It was the object of the present invention to provide an economic process for producing Guerbet alcohols, wherein waste water usually obtained during conventional purification is completely avoided and which yields metal- and soap-free products.

The subject matter of the present invention is a process for producing high-purity Guerbet alcohols, particularly soap- and heavy metal-free Guerbet alcohols, by condensation of primary and/or secondary alcohols having 2 to 30 carbon atoms in the presence of one or more alkaline catalyst(s) and/or one or more heavy metal catalyst(s), wherein the reaction product is directly split up by distillation, i. e. without any different intermediate purification steps, yielding product alcohol and educt alcohol (starting alcohol), if any, on the one hand and catalyst/catalyst mixture and higher-molecular products, if any, on the other hand, and in which the reaction product can be removed batchwise or continuously from the reaction space.

The reaction product is directly led to the distillation stage without any preceding washing, filtration, centrifugation, steam distillation or other purification steps. The bottoms produced during distillation are highly viscous at room temperature and can readily be disposed of.

It was surprisingly found that according to the process of the invention it is possible to free the reaction mixture obtained by Guerbet reaction from heavy metal ions and alkaline catalyst residues in a simple and economic way by distilling the crude reaction product. Thus, no waste water is produced and loading of waste water with heavy metal ions is prevented. The co-catalysts used are commercially available heavy metal salts. It is not necessary to use any supported compounds. Furthermore, products not containing any heavy metals are obtained which is highly important when said products are to be used in pharmaceuticals and cosmetics.

DESCRIPTION OF THE PREFERRED EMBODIMENTS

According to this invention, primary and/or secondary, linear or cyclic alkanols having 2 to 30 carbon atoms and alkanols having a methylene group in α-position to the carbon atom bearing the hydroxyl group are reacted to yield the desired Guerbet alcohols which are essentially free from higher-molecular condensation products. Such alkanols used as educts can be represented by the general formula

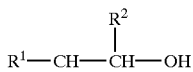

wherein the residues $R^1$ and $R^2$ can be a hydrogen atom, an aryl residue or a straight-chain or branched alkyl group, and $R^1$ and $R^2$ can be the same or different. Favorable starting materials are those educts wherein $R^1$ represents an alkyl group and $R^2$ is a hydrogen atom, i.e. primary alkan-1-ols. Typical examples of said alkanols each having a terminal OH function are ethanol, propanol, isopropyl alcohol, butanol, pentanol, hexanol, octanol, decanol, undecanol, dodecanol, tridecanol, tetradecanol, pentadecanol, hexadecanol, octadecanol, eicosanol, docosanol, tetracosanol, hexacosanol, octacosanol, and triacontanol, and, furthermore, secondary alkanols, such as 4-methylpentan-2-ol, hexan-2-ol, octan-2-ol, cyclopentanol, cyclohexanol and the corresponding isomers of the primary alkanols mentioned hereinabove.

The educts mentioned hereinabove can be synthetic products, e. g. Ziegler alcohols or oxoalcohols, or natural products. Particularly preferred starting materials are straight-chain primary alkanols having 6 to 22 carbon atoms. Typical examples are caproic-, oenanthic-, capryl-pelargonic-, caprinic-, lauryl-, myristyl-, cetyl-, stearyl-, arachidyl-, and behenyl alcohol.

Said starting materials can also be used as technical-grade mixtures with other alcohols which is common practice in fats chemistry.

Suitable catalysts for the process of the invention are those known in the art. Among alkaline catalysts, the oxides, hydroxides, and alcoholates of the alkali metals lithium, sodium, potassium, and cesium are particularly suitable. Potassium hydroxide and/or cesium hydroxide are particularly preferred.

Suitable co-catalysts for the process of the invention are those known in the art which are listed for example in DE A1 24 00 326.

Said co-catalysts can be used in quantities of 0.05 to 3.0 grams per mol, referring to the total amount of alcohol used.

According to this invention, soap and heavy metals are separated from the crude Guerbet alcohols without the washing treatment usually performed in the art or steam distillation (see U.S. Pat. No. 2,457,866). The term 'washing treatment' means treating the crude Guerbet alcohols with an excess of aqueous solutions to eliminate by-products and soaps. Such treatment produces a large amount of waste water loaded with metals and organic solvents. Furthermore, according to the process of the invention, no filtration, extraction, or centrifugation is necessary.

The optimum temperature for producing Guerbet alcohols according to this invention depends on the type of starting alcohol. Normally, the reaction will yield good results when it is conducted at the boiling temperature of the alcohol. Even temperatures of as low as approximately 180° C. will give satisfactory results, but the preferred temperature according to this invention is from 200 to 320° C., particularly from 250 to 320° C., occasionally up to 350° C. in order to eliminate the reaction water as rapidly as it is formed from the reaction equilibrium. High conversions and yields are thus achieved. The maximum allowable temperature is the temperature at which starting alcohol or reaction product start to decompose. Usually, the temperature limit is between about 350° C. and 400° C. A reaction temperature of 250 to 320° C. in the reaction mixture is normally sufficient to give good results.

The reaction is usually carried out at atmospheric pressure. If, however, the boiling point of the starting alcohol is below the optimum reaction temperature, the reaction can also be performed in a closed system at pressures of up to 30 bar. Preferably, the pressure should be high enough to keep the reaction system liquid. When carrying out the reaction in a closed system at elevated pressure, it is important that all of the water formed during the reaction be immediately eliminated in order to ensure high yields. When using long-chain alcohols, e. g. tetradecanol, the reaction water must be removed under vacuum. The reaction time does not require special consideration and can be varied in a wide range, provided there is sufficient time to allow formation of dimers. On the other hand, the reaction time should not be too long, thereby preventing formation of trimers as a result of continuing condensation. Normally, the average residence time is from 0.5 to 4 hours, the preferred reaction time being between 1.5 and 3 hours at a given temperature, pressure, and catalyst concentration.

The reaction mixture is purified by distillation. In contrast to prior art processes, the bottoms stay liquid, thus being pumpable. Additionally, it is advantageous that the reboiler cannot get plugged with solids, thereby avoiding cleaning procedures. The overall yields of valuable products, recyclable front-end alcohol, and Guerbet alcohol increase in each of the process steps. The distillation residue can readily be disposed of.

The distillation is carried out in at least two stages, wherein in the first stage primarily educt alcohol is separated by flash distillation, the reactor effluent thereby being preferably distilled essentially without any supply of thermal energy and at essentially unchanged temperature. In the second stage, primarily product alcohol and catalyst are separated from each other, preferably by thin-layer or molecular distillation.

The average hold-up time of the reaction product in the distillation apparatus(es) until the catalyst or catalyst mixture is separated is preferably 0.1 to 10 minutes, most preferably less than 6 minutes. In addition, the distillation is preferably carried out in one of the distillation stages, most preferably in both stages, at a vacuum of 1 to 100 mbar, most preferably 5 to 50 mbar, and temperatures of 200 to 320° C. The distillation is preferably carried out such that the remaining catalyst bottoms are liquid and pumpable at temperatures of greater than 200° C.

In order to prevent formation of by-products, the reaction is discontinued by distilling off the organic compounds from the crude product within the shortest possible time which is technically feasible.

In said distillation step the crude product leaving the reactor is preferably split up at first by flash distillation into a monomeric alcohol fraction (educt) and a dimeric alcohol fraction (product). During flash distillation the gaseous phase is withdrawn after the equilibrium between liquid phase and vapor phase has been established. The vaporous monomer fraction (the educt alcohol which is unsubstituted in the beta position) is condensed, slightly supercooled and directly returned to the reactor. The alkaline dimer fraction which stays liquid during flash distillation is distilled in a thin-layer evaporator in order to separate alkaline by-products. The term 'thin-layer distillation' used herein includes film distillation, falling-film distillation, and molecular distillation (short-path or open-path distillation). In thin-layer evaporation the liquid to be evaporated is mechanically distributed, e. g. by gravitation, centrifugal force, or mechanical wipers, thereby forming thin layers which are less than 0.3 mm, preferably less than 0.2 mm thick and which are evaporated at reduced pressure.

The preferred residence time during flash distillation is 0.1 to 5 minutes, while the distillation temperature is preferably 200 to 320° C. at 5 to 100 mbar. When utilizing thin-layer or molecular distillation, the preferred residence time is 0.1 to 5 minutes, while the distillation temperature is preferably 200 to 320° C. at 5 to 100 mbar.

After leaving the thin-layer evaporator, the alkaline by-products which are essentially free from dimeric alcohol are cooled to ambient temperature un[0084] disposed of as highly viscous material.

After leaving the thin-layer evaporator, the dimeric fraction which is no longer alkaline is condensed and, optionally, further purified by distillation, e. g. by conventional fractional distillation, whereby a light intermediate fraction and higher organic compounds are obtained as by-products. The monomeric alcohol obtained as well is returned to the reaction stage.

EXAMPLES

1. Production of 2-Butyloctanol from 1-Hexanol

The process was conducted under the conditions described hereinabove yielding crude Guerbet alcohol. The product was continuously charged without cooling to a flash apparatus thereby reducing the pressure to 50 mbar. While the equilibrium temperature established in the flash apparatus, most of the hexan-1-ol was removed overhead and returned to the reaction stage. The residence time in the flash apparatus was set to less than 5 minutes..

The alkaline dimeric fraction containing the catalyst was directly charged to a thin-layer evaporator wherein at a pressure of 30 mbar and temperatures of 250 to 290° C. the reaction product was liberated from the catalyst system, higher oligomers, and metal soaps.

The bottoms thus obtained were free from 1-hexanol and 2-butyloctanol and, by employing the distillation conditions described hereinabove, they were obtained as a pumpable liquid which was discharged, cooled, and disposed of as a highly viscous material. 2-Butyloctanol was obtained in high yields as a metal- and alkali-free product of value.

2. Production of 2-Octyldodecanol from 1-Decanol

The process was conducted under the conditions described hereinabove yielding crude Guerbet alcohol. The product was continuously charged without cooling to a flash apparatus thereby reducing the pressure to 50 mbar. While the equilibrium temperature established in the flash apparatus, most of the 1-decanol was removed overhead and returned to the reaction stage. The residence time in the flash apparatus was set to less than 5 minutes.

The alkaline dimeric fraction containing the catalyst was directly charged to a thin-layer evaporator wherein at a pressure of 5 mbar and temperatures of 250 to 290° C. the reaction product was liberated from the catalyst system, higher oligomers, and metal soaps.

The bottoms thus obtained were free from 1-decanol and 2-octyldodecanol and, by employing the distillation conditions described hereinabove, they were obtained as a pumpable liquid which was discharged, cooled, and disposed of as a highly viscous material. 2-octyldodecanol was obtained in high yields as a metal- and alkali-free product of value.

What is claimed is:

1. In a process for producing purified Guerbet alcohols by condensation of primary and or secondary alcohols having 2 to 30 carbon atoms in the presence of at least one alkaline catalyst and/or at least one heavy metal catalyst wherein a reaction mixture comprising product alcohol is produced the improvement comprising:

introducing the reaction mixture produced directly to a first-stage distillation, distilling said reaction mixture in said first-stage distillation to separate at least a portion of the primary and/or secondary alcohols having 2 to 30 carbon atoms from said reaction mixture and produce a first-stage distillation product; and distilling said first-stage distillation product in a second-stage distillation to separate said first stage distillation product from at least one alkaline catalyst residues and/or at least one heavy metal catalyst residue to produce an overhead product Guerbet alcohol stream and a bottoms stream wherein the first stage distillation is a flash distillation and the process does not involve an intermediate washing treatment to separate said at least one alkaline catalyst residue and/or said at least one heavy metal catalyst residue.

2. The process according to claim 1, wherein the average residence time of the reaction mixture in the first distillation stage is 0.1 to 10 minutes.

3. The process according to claim 2 wherein the average residence time is 0.1 to 6 minutes.

4. The process according to claim 1 wherein said second-stage distillation is a thin layer or molecular distillation.

5. The process according to claim 1, wherein a vacuum of 1 to 100 mbar and temperatures of 200 to 320° C. are utilized in said first-stage distillation.

6. The process according to claim 5 wherein the temperature in said second-stage distillation is from 200 to 320° C.

7. The process according to claim 1, wherein a vacuum of 1 to 100 mbar and temperatures of 200 to 320° C. are utilized in said second-stage distillation.

8. The process according to claim 7, wherein the temperature in said first-stage distillation is 200 to 320° C.

9. The process according to any of claims 5 or 7 wherein the vacuum is from 5 to 50 mbar.

10. The process according to claim 1, wherein the bottoms stream from the second-stage distillation is maintained at a temperature of 200° C. or greater.

11. The process according to claim 1, wherein the overhead product Guerbet alcohol stream is subjected to fractional distillation.

12. The process according to claim 1 wherein the condensation of the primary and/or secondary alcohols is conducted at a temperature of 200 to 320° C. and pressures of 50 mbars to 30 bars.

13. The process according to claim 1 wherein said primary and/or secondary alcohols comprise straight-chain, primary, or cyclic alcohols having 6 to 22 carbon atoms.

* * * * *

UNITED STATES PATENT AND TRADEMARK OFFICE
CERTIFICATE OF CORRECTION

PATENT NO.    : 6,419,797 B1
DATED         : July 16, 2002
INVENTOR(S)   : Erich Scherf et al.

It is certified that error appears in the above-identified patent and that said Letters Patent is hereby corrected as shown below:

<u>Title page,</u>
Item [73], delete "Säsol" and insert therefor -- Sasol --

<u>Column 3,</u>
Lines 5-10, delete "$R^1-CH-CHR^2-OH$" and insert therefor
-- $R^1-CH_2-CHR^2-OH$ --

Signed and Sealed this

Seventh Day of October, 2003

JAMES E. ROGAN
*Director of the United States Patent and Trademark Office*